(12) United States Patent
Muhanna et al.

(10) Patent No.: US 6,824,565 B2
(45) Date of Patent: Nov. 30, 2004

(54) SYSTEM AND METHODS FOR INSERTING A VERTEBRAL SPACER

(76) Inventors: Nabil L. Muhanna, 2128 Valley Rd., Gainesville, GA (US) 30501; David L. Schalliol, 4611 Circle Dr., Oakwood, GA (US) 30566

( * ) Notice: Subject to any disclaimer, the term of this patent is extended or adjusted under 35 U.S.C. 154(b) by 85 days.

(21) Appl. No.: 09/947,851

(22) Filed: Sep. 6, 2001

(65) Prior Publication Data

US 2002/0045944 A1 Apr. 18, 2002

Related U.S. Application Data

(60) Provisional application No. 60/231,142, filed on Sep. 8, 2000.

(51) Int. Cl.$^7$ ................................................ A61B 17/58
(52) U.S. Cl. ..................................................... 623/17.16
(58) Field of Search ............................. 606/99, 86, 84, 606/82, 79; 623/17.11–17.16

(56) References Cited

U.S. PATENT DOCUMENTS

| | | | |
|---|---|---|---|
| 3,875,595 A | 4/1975 | Froning | |
| 4,349,921 A | 9/1982 | Kuntz | |
| 4,479,491 A | 10/1984 | Martin | 128/92 |
| 4,599,086 A | 7/1986 | Doty | |

(List continued on next page.)

FOREIGN PATENT DOCUMENTS

| WO | WO 99/11203 | 3/1999 | A61F/2/44 |
|---|---|---|---|

OTHER PUBLICATIONS

Tsantrizos et al., *A Comparative Biomechanical Study of Posterior Lumbar Interbody Fusion Implants*, 1997 Masters Thesis, Orthopaedic Research Laboratory, Division of Orthopaedic surgery McGill University, Montreal, Qc, Canada, The Uniformed Services, University of the Health Sciences, Bethesda, Maryland, U.S.A.

Collis et al., *Anterior Total Disc Replacement: A Modified Anterior Lumar Interbody Fusion*, Lumbar Interbody Fusion, Chapter 13, pp. 149–152.

Medical Multimedia Group, *A Patient's Guide to Low Back Pain*, www.sechrest.com/mmg/back/backpain.html, pp. 1–15, Jun. 8, 1998.

Northwest Spine Surgery, *BAK Interbody Fusion* . . . , www.backsurgery.com/bak1.htm, pp. 1–2, ©1998.

J. Flood—*Titanium cage lumbar interbody fusion*, ©1997, 1998—Web Site.

(List continued on next page.)

*Primary Examiner*—Kevin Shaver
*Assistant Examiner*—Michael B. Priddy
(74) *Attorney, Agent, or Firm*—Womble Carlyle Sandridge & Rice, PLLC

(57) ABSTRACT

The present invention provides vertebral spacers having a lower surface and an upper surface, an anterior face and a posterior face extending from the lower surface, and at least one guiding groove for engaging an insertion tool. A system for delivering a vertebral spacer to the spinal column of a patient, includes an insertion tool, an optional guiding tool, a pusher, a vertebral spacer, and a cutting tool. The insertion tool accepts any of a pusher, a vertebral spacer, or a cutting tool and has at least one spacer guide for engaging with a guiding groove of a vertebral spacer. The vertebral spacer is inserted into a patient by inserting the insertion tool into an intervertebral space, engaging the guiding groove of a vertebral spacer with a space guide of the insertion tool, advancing a pusher into the insertion tool, thereby pushing the vertebral spacer into the intervertebral space and thereafter removing the pusher and the insertion tool. The cutting tool is optionally used to chisel at least one vertebral space receiving slot in the vertebrae. A hardening biocompatible composition also maybe delivered, to bond the vertebral spacer to an adjacent vertebra or be an osteogenic composition to promote bone growth.

47 Claims, 14 Drawing Sheets

U.S. PATENT DOCUMENTS

| | | | | |
|---|---|---|---|---|
| 4,834,757 | A | 5/1989 | Brantigan | |
| 4,878,915 | A | 11/1989 | Brantigan | |
| 5,314,477 | A | 5/1994 | Marnay | |
| 5,320,644 | A | 6/1994 | Baumgartner | 623/17 |
| 5,397,364 | A | 3/1995 | Kozak et al. | 623/17 |
| 5,425,772 | A | 6/1995 | Brantigan | 623/17 |
| 5,484,437 | A | 1/1996 | Michelson | 606/61 |
| 5,499,984 | A * | 3/1996 | Steiner et al. | 606/80 |
| 5,609,636 | A | 3/1997 | Kohrs et al. | 623/17 |
| 5,674,296 | A | 10/1997 | Bryan et al. | |
| 5,693,100 | A | 12/1997 | Pisharodi | 623/17 |
| 5,722,977 | A | 3/1998 | Wilhelmy | 606/84 |
| 5,755,798 | A | 5/1998 | Papavero et al. | 623/17 |
| 5,776,196 | A | 7/1998 | Matsuzaki et al. | 623/17 |
| 5,776,197 | A | 7/1998 | Rabbe et al. | 623/17 |
| 5,782,919 | A | 7/1998 | Zdeblick et al. | 623/17 |
| 5,865,848 | A | 2/1999 | Baker | 623/17 |
| 5,916,267 | A | 6/1999 | Tienboon | 623/17 |
| 5,961,554 | A | 10/1999 | Janson et al. | 623/17 |
| 5,989,291 | A | 11/1999 | Ralph et al. | 623/17 |
| 6,004,326 | A * | 12/1999 | Castro et al. | 606/99 |
| 6,030,390 | A | 2/2000 | Mehdizadeh | 606/84 |
| 6,033,438 | A | 3/2000 | Bianchi et al. | 623/17 |
| 6,056,749 | A | 5/2000 | Kuslich | 606/61 |
| 6,059,790 | A | 5/2000 | Sand et al. | 606/99 |
| 6,096,080 | A | 8/2000 | Nicholson et al. | |
| 6,120,506 | A * | 9/2000 | Kohrs et al. | 606/80 |
| 6,140,452 | A | 10/2000 | Felt et al. | |
| 6,146,422 | A | 11/2000 | Lawson | |
| 6,224,607 | B1 * | 5/2001 | Michelson | 606/96 |
| 6,283,966 | B1 * | 9/2001 | Houfburg | 606/61 |
| 6,368,325 | B1 * | 4/2002 | McKinley et al. | 606/99 |
| 6,395,032 | B1 | 5/2002 | Gauchet | |
| 6,520,967 | B1 * | 2/2003 | Cauthen | 606/99 |
| 2001/0039458 | A1 | 11/2001 | Boyer, II et al. | |

OTHER PUBLICATIONS

Sulzer Spine–Tech—The BAK™ Patient Information, *An Innovative Approach to Surgical Spinal Treatment*, http://www.spine-tech.com/BAK–IPSIndex.html, May 22, 2000.

Sulzer Spine–Tech—The BAK© Patient Information, *About BAK* pp. 1–2, http://www.spine-tech.com/BAK–IPSIndex.html, May, 22, 2000.

Sulzer Spine–Tech—The BAK™ Patient Information, *How BAK Works*, http:www.spine-tech.com/BAK–IPSIndex.html, May 22, 2000.

Sulzer Spine–Tech—The BAK™ Patient Information, *Clinical Results, Prospective Multi–Center Clinical Trial of the BAK™ Fusion System*, pp. 1–18, http:// www.spine-tech.com/BAK–IPSIndex.html, May 22, 2000.

Dimar et al., *Posterior Lumbar Interbody Cages Do Not Augment Segmental Biomechanical Stability*, American Academy of Orthopedic Surgeons, 67$^{th}$ Annual Meeting, Mar. 17, 2000.

Sengupta et al., *Biomechanical Comparison of Stability Provided by Rectangular vs Cylindrical Interbody Fusion Cages*, Date of Publication Unavailable.

Experience and Short–Term Results with No–React Cardiovasular Implants—Chapter 15—Advances in Anticalcific and Antidegenetative Treatment of Heart Valve Bioprstheses, First Edition, edited by Shlomo Gabbay, M.D., David J. Wheatley, M.D., Silent Partners, Inc, Austin, 1997.

Structure of The Human Intervertebral Disk—Diwan et al.—Current Concepts in Intervertebral Disk Restoration—pp. 454–464.

REVIEW—The Artificial Disc: Theory, Design and Materials—Qi–Bin Bao et al.—Biomaterials 1998—pp. 1157–1167.

Shelhigh DuraShield—No–React Treated, Dural Repair Patch—Shelhigh, Inc.—0318.

Unsurpassed Cytocompatibility Carotid and Periheral Vascular Patch—Shelhigh No–React VascuPatch—Shelhigh, Inc.

Shelhigh, Inc.—Handling and Instruction for Use—No–React/Detoxified/Dura Shield—Product No. 555–DS.

Shelhigh No React Patch—p. 1 of 1—Dec. 6, 2000.

Pelvicol Acellular Collagen Matrix—Surgical Innovations Tissue Solutions—BARD.

No–React Detoxification Process: A Superior Anticalcification Method for Bioprostheses Abolhoda, M.D. et al.—1996—The Society of Thoracic Surgeons—Published by Elsevier Science, Inc.—pp. 1724–1730.

Calcification of Bovine Pericardium: Glutaraldehyde Versus No–React Biomodiciation—Abolhoda, M.D. et al.—1996–1996—The Society of Thoracic Surgeons—Published by Elsevier—pp. 169–174.

Shelhigh N–React—Pericardial Patch—Clinical Results—Shelhigh, Inc.—0318.

* cited by examiner

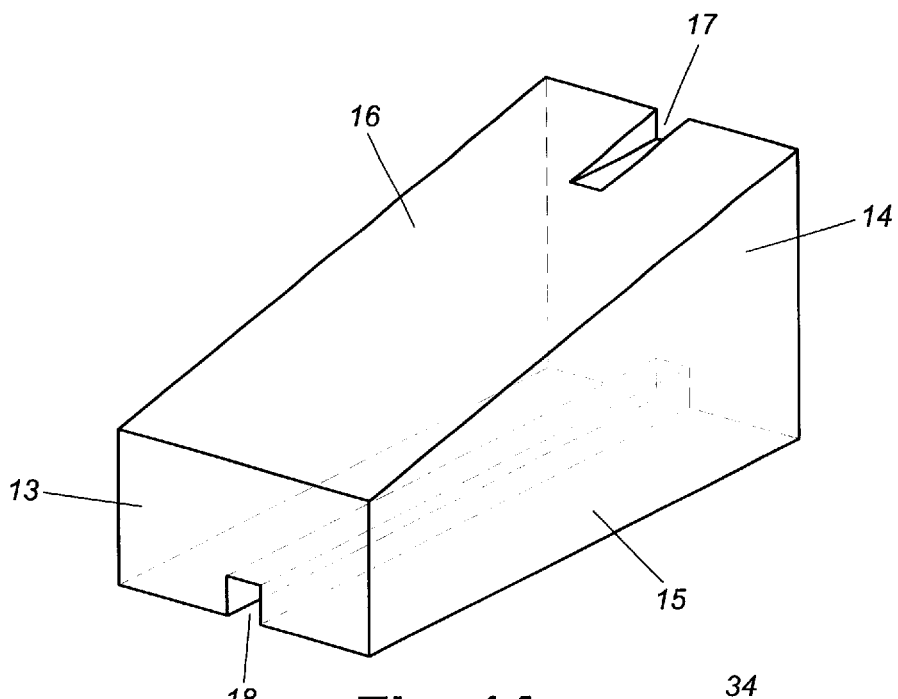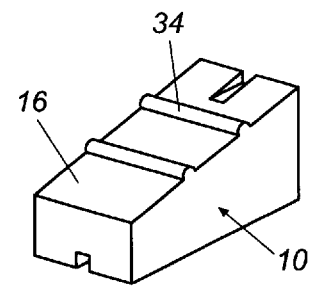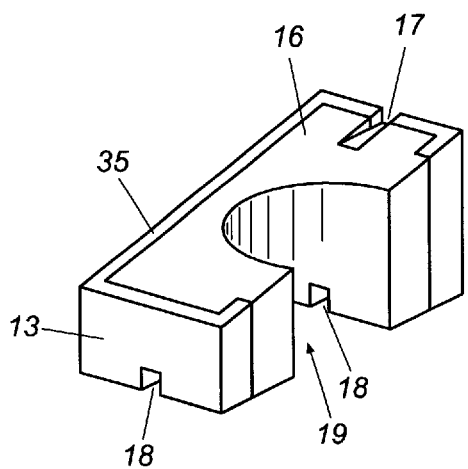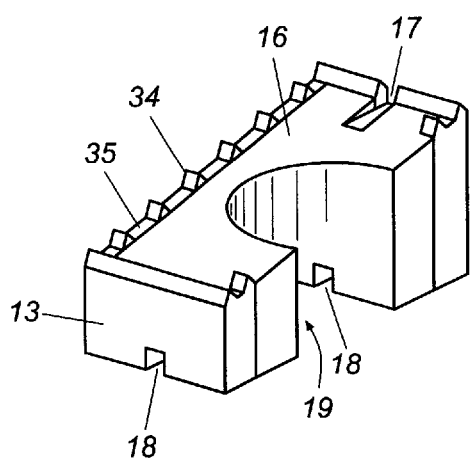
Fig. 1A
Fig. 1B
Fig. 2A
Fig. 2B

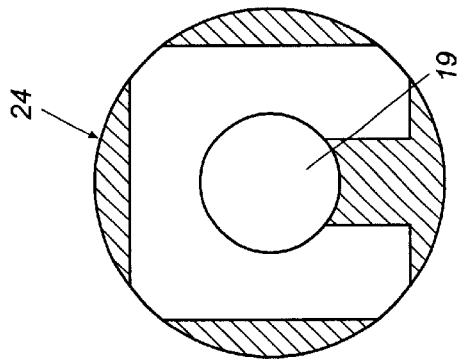
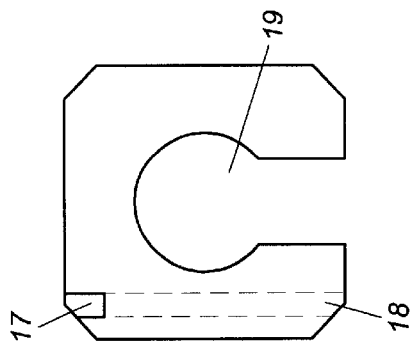
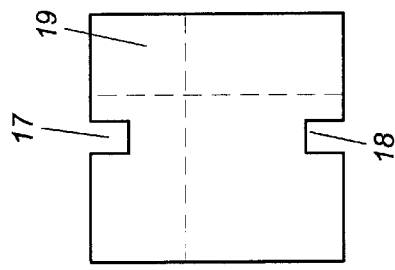
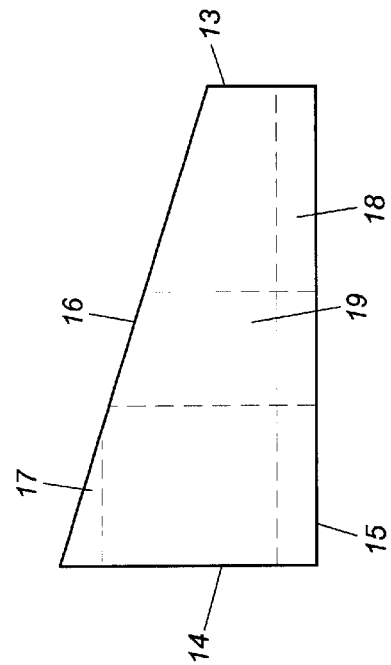
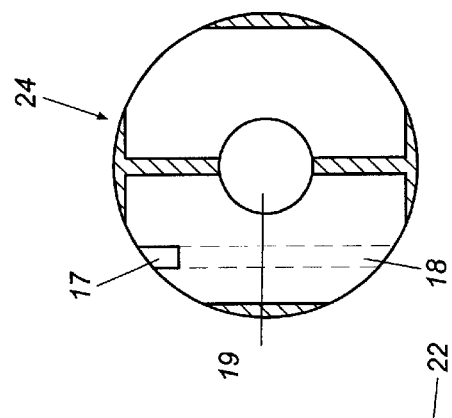
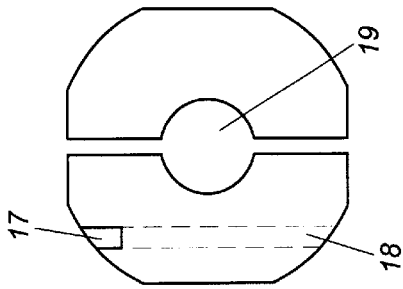
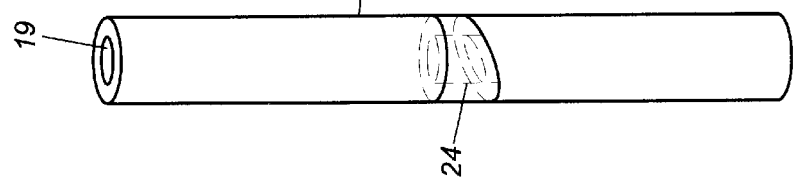

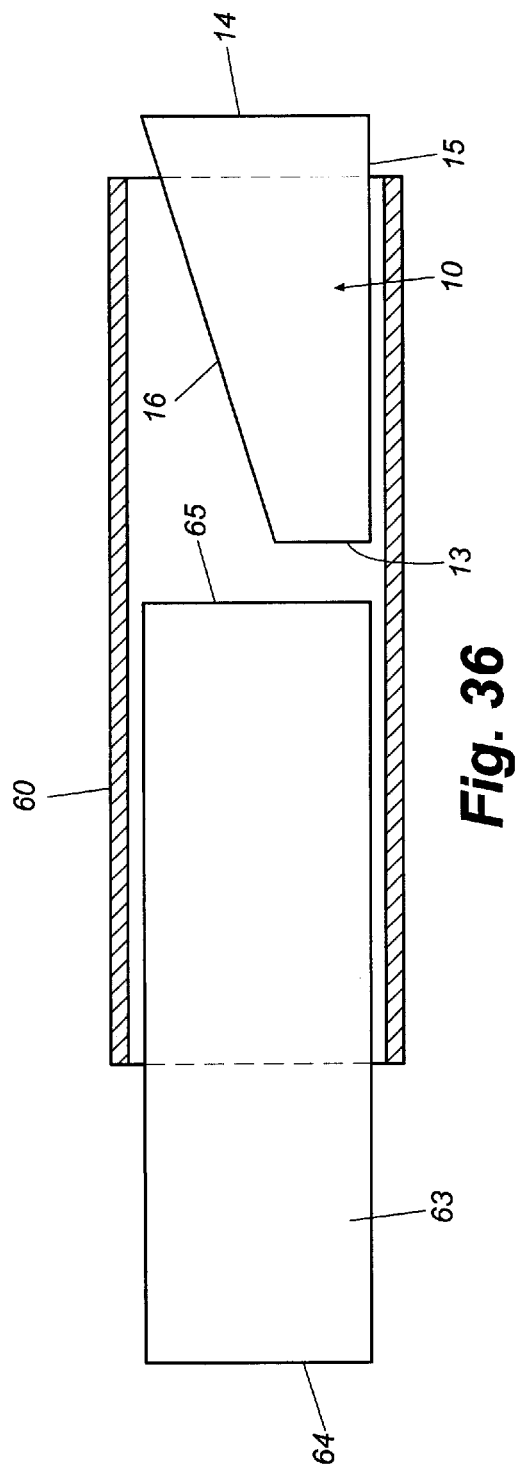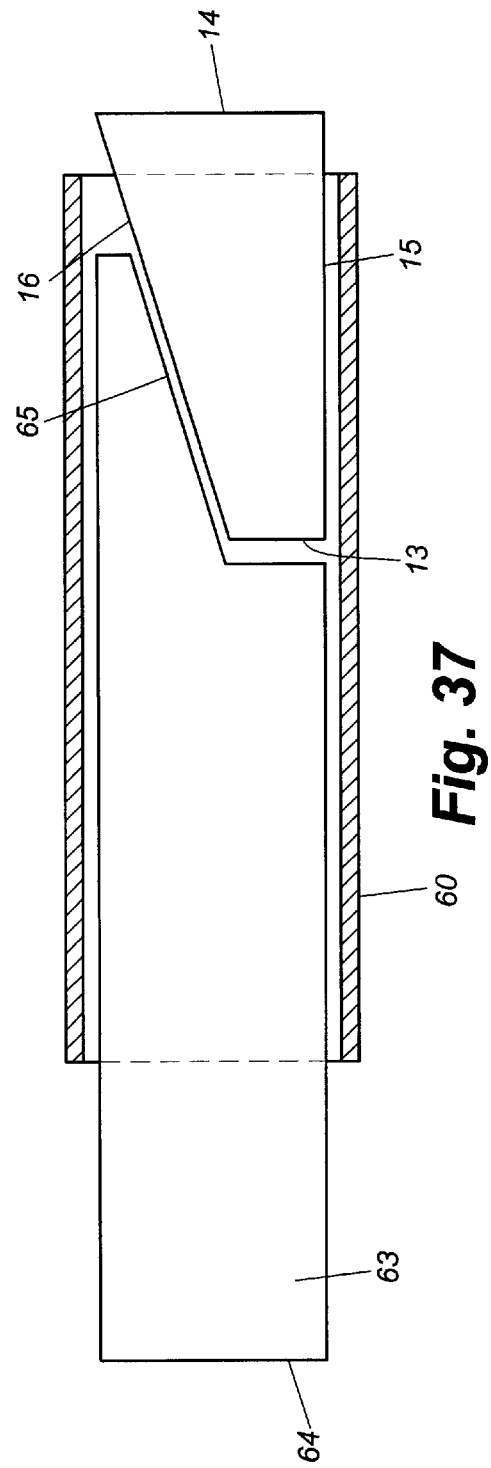

SYSTEM AND METHODS FOR INSERTING A VERTEBRAL SPACER

The present application claims the benefit of the provisional U.S. Application Ser. No. 60/231,142 filed Sep. 8, 2000, which is incorporated herein by reference in its entirety.

FIELD OF INVENTION

The present invention generally relates to a vertebral spacer to be inserted into an intervertebral space, thereby supporting the spinal column of a patient. The present invention further relates to a system and methods for implanting the vertebral spacer into the spinal column and securing the spacer therein.

BACKGROUND OF THE INVENTION

The spinal column, which is the central support to the vertebrate skeleton and a protective enclosure for the spinal cord, is a linear series of vertebral bones. Intervertebral discs separate and reduce friction between adjacent vertebrae and absorb compression forces applied to the spinal column. Spinal nerves that extend from each side of the spinal cord exit the column at intervertebral forama.

A typical vertebra comprises an anterior body, and a posterior arch that surrounds the spinal cord lying within the vertebral foramen formed by the arch. The muscles that flex the spine are attached to three processes extending from the posterior arch. On the upper surface of each vertebra in a standing human, are two superior articulated processes that oppose two inferior articulated processes extending from the lower surface of an adjacent vertebra. Facets on the opposing processes determine the range and direction of movement between adjacent vertebrae, hence the flexibility of the spinal column.

The intervertebral discs include the fibrillar cartilage of the anulus fibrosus, a fibrous ring, the center of which is filled with an elastic fibrogelatinous pulp that acts as a shock absorber. The outer third of the anulus fibrosus is innervated. The entire spinal column is united and strengthened by encapsulating ligaments.

Back pain is one of the most significant problems facing the workforce in the United States today. It is a leading cause of sickness-related absenteeism and is the main cause of disability for people aged between 19 and 45. Published reports suggest that the economic cost is significant, treatment alone exceeding $80 billion annually. Although acute back pain is common and typically treated with analgesics, chronic pain may demand surgery for effective treatment.

Back pain can occur from pinching or irritation of spinal nerves, compression of the spine, vertebral shifting relative to the spinal cord axis, and bone spur formation. The most common cause of disabling back pain, however, stems from trauma to a intervertebral disc, resulting from mechanical shock, stress, tumors or degenerative disease, which may impair functioning of the disc and limit spinal mobility. In many cases, the disc is permanently damaged and the preferred treatment becomes partial or total excision.

Another cause of back injury is herniation of the intervertebral disc, wherein the gelatinous fluid of the nucleus pulposus enters the vertebral canal and pressures the spinal cord. Again, surgery is often the only method available for permanent relief from pain or the neurological damage ensuing from the pressure of fluid on the spinal cord, and requires replacement of the damaged disc.

Traumatic injury to an intervertebral disc that is not removed will frequently promote scar tissue formation. Scar tissue is weaker than original healthy tissue so that the disc will progressively degenerate, lose water content, stiffen and become less effective as a shock absorber. Eventually, the disc may deform, herniate, or collapse, limiting flexibility of the spinal column at that position. The only option is for the intervertebral disc to be partially or totally removed.

When the disc is partially or completely removed, it is necessary to replace the excised material to prevent direct contact between hard bony surfaces of adjacent vertebrae. One vertebral spacer that may be inserted between adjacent vertebrae, according to U.S. Pat. No. 5,989,291 to Ralph et al., includes two opposing plates separated by a belleville washer or a modified belleville washer. The washer functions to provide a restorative force to mimic the natural functions of the disc of providing a shock absorber and mobility between adjacent vertebrae. However, mechanical devices intended to replicate intervertebral disc function have had only limited success. An alternative approach is a "cage" that maintains the space usually occupied by the disc to prevent the vertebrae from collapsing and impinging the nerve roots.

Spinal fusion may be used to restrict motion occurring between two vertebrae due to spinal segmental instability. Fusing the vertebrae together, however, reduces the mechanical back pain by preventing the now immobile vertebrae from impinging on the spinal nerve. The disadvantage of such spacers is that stability is created at the expense of spinal flexibility.

Surgical procedures for replacing intervertebral disc material, rather than the fusing of the vertebrae, have included anterior approaches and posterior approaches to the spinal column. The posterior approach (from the back of the patient) encounters the spinous process, superior articular process, and the inferior articular process that must be removed before insertion of the disc replacement material into the intervertebral space. Excessive removal of the bony process triggers further degradation and impediment of the normal movement of the spine. The anterior approach to the spinal column is complicated by the internal organs that must be bypassed or circumvented to access the vertebrae.

Many intervertebral spacers require preparation of the surfaces of the adjacent vertebrae to accommodate the spacer, causing significant tissue and bone trauma. For example, chiseling or drilling of the vertebral surface may be required to prepare a receiving slot. They may also require screwing the spacer into the intervertebral space, making installation difficult and increasing trauma to the vertebral tissue. Many spacers include complex geometries and are costly to manufacture. Examples of such geometrically complex spacers are described in U.S. Pat. No. 5,609,636 to Kohrs et al., U.S. Pat. No. 5,780,919 to Zdeblick et al., U.S. Pat. No. 5,865,848 to Baker and U.S. Pat. No. 5,776,196 to Matsuzaki et al. Many of these complex spacers may require screwing the spacer into the intervertebral space, thereby making installation difficult and traumatic to the vertebral tissue.

SUMMARY OF THE INVENTION

There is a need for a vertebral spacer having a simple geometry that is easily insertable into an intervertebral space while causing minimal trauma to the surface of the vertebrae as well as the bony processes thereof. The present invention provides a vertebral spacer having a simple geometry for supporting adjacent vertebrae after excision, at least partially or wholly, of an intervertebral disc. The spacer includes a body having a lower surface and an upper surface. The lower surface will be supported by a lower vertebra; the upper surface supports the adjacent upper vertebra. The body of the vertebral spacer of the present invention, therefore, provides support between the two adjacent vertebrae and to the spinal column.

The body of the vertebral spacer of the present invention additionally has an anterior face and a posterior face extending from the lower surface. The height of the anterior face of the body may be less than, or greater than, the height of the posterior face to maintain the curvature of the spine when the vertebral spacer is inserted between two vertebrae. The body of the vertebral spacer also includes at least one guiding groove suitable for engaging with an insertion tool for delivering the vertebral spacer to an intervertebral space.

The present invention further provides a system for delivering a vertebral spacer to the spinal column of a patient, comprising an insertion tool with a channel; (b) an optional guiding tool for directing the insertion tool to a selected point of insertion of a vertebral spacer; (c) a pusher; (d) a vertebral spacer slideably disposed in the channel of the insertion tool; and (e) a cutting tool. The cutting tool can be slid into the channel of the insertion tool providing that the pusher and the vertebral spacer are not therein.

The channel of the insertion tool is configured to slideably accept any of a vertebral spacer, a pusher, a vertebral spacer, or a cutting tool. The insertion tool further comprises a spacer guide or a plurality of spacer guides for engagement with a first guiding groove or a second guiding groove of a vertebral spacer.

In one embodiment of the insertion tool the spacer guide is a flange extending from the channel. In another embodiment, the spacer guide is two opposing flanges configured to slideably engage with a first guiding groove and a second guiding groove, respectively.

In another embodiment of the insertion tool, the spacer guide is at least one rib longitudinally placed on the inner surface of the channel of the insertion tool.

Other embodiments of the insertion tool of the present invention include spacer guides that may be, but are not limited to, a segmented longitudinal rib, or a linear series of protrusions, also on the inner surface of the channel.

The present invention further provides a method for delivering a vertebral spacer to a patient, comprising the steps of inserting the insertion tool into an intervertebral space of the spinal column of a patient, engaging at least one guiding groove of a vertebral spacer with a space guide of the insertion tool, sliding a pusher into the channel of the insertion tool, advancing the pusher and thereby pushing the vertebral spacer into the intervertebral space and removing the pusher and the insertion tool from the patient.

The method of the present invention may further comprise the optional step of inserting a guiding tool into an intervertebral space for directing the insertion tool into the intervertebral space. The insertion tool may be slid along the guide tool to a selected position suitable for insertion of a vertebral spacer in the intervertebral space. The guide tool is then extracted from the insertion tool leaving the insertion tool inserted between adjacent vertebrae.

The cutting tool is optionally slid along the channel of the insertion tool to engage a vertebra and generally is used to chisel at least one vertebral space receiving slot in the vertebrae. The cutting tool is removed from the patient by sliding the cutting tool back through the channel of the insertion tool. A vertebral spacer may then be slideably engaged with the insertion tool, with a space guide on the insertion tool engaging with a guiding groove of the vertebral spacer. The pusher may be engaged and advanced along the channel, thereby delivering the vertebral spacer into the vertebral spacer receiving slot (or receiving slots) in the adjacent vertebrae. It is also contemplated that a vertebral spacer receiving slot may not be cut in the adjacent vertebrae and that the inserted vertebral spacer optionally may contact only the uncut surface of the vertebrae.

One embodiment of the method of the present invention comprises the additional step of delivering a hardening biocompatible composition to the vertebral spacer. The hardening biocompatible composition may be used, for example, to bond the vertebral spacer to an adjacent vertebra or be an osteogenic composition to promote bone growth from the adjacent vertebrae into the vertebral spacer. The hardening biocompatible composition can be, for example, an organic polymer, a mineral composition such as a hydroxyapatite-based composition, methyl methacrylate, or the like, or a combination thereof. A hydroxyapatite-based composition is especially useful in the context of the present invention for promoting osteocyte growth and bone deposition.

Various objects, features, and advantages of the invention will become more apparent upon review of the detailed description set forth below when taken in conjunction with the accompanying drawing figures, which are briefly described as follows.

BRIEF DESCRIPTION OF THE FIGURES

FIG. 1A illustrates an embodiment of the vertebral spacer according to the present invention having a first guiding groove and a second guiding groove.

FIG. 1B illustrates an embodiment of the vertebral spacer according to the present invention having protrusions on the upper surface thereof.

FIG. 2A illustrates an embodiment of the vertebral spacer according to the present invention wherein a section dissected from a femur bone is contained within a partial metallic sheath.

FIG. 2B illustrates an embodiment of the vertebral spacer according to the present invention wherein a section dissected from a femur bone is contained within a partial metallic sheath and having angular protuberances on the metallic sheath.

FIGS. 10–12 illustrate the sectioning of a femur to give at least one vertebral spacer according to the present invention.

FIG. 10 shows the sectioning planes for the excision of a section of a femur.

FIG. 11 shows a cross-sectional view of an excised section of a femur with minimal portions of the femur shown in cross-hatch trimmed away to give two vertebral spacers.

FIG. 12 shows the cross-sectional view of two vertebral spacers cut from a femoral section.

FIG. 13 shows an end elevation of a vertebral spacer according to the present invention excised from a femur and having two guiding grooves therein.

FIG. 14 shows a side elevation of a vertebral spacer according to the present invention excised from a femur.

FIGS. 15 and 16 illustrate an embodiment of the vertebral spacer of the present invention excised from a femur wherein the femur medullary cavity not bisected.

FIG. 23 shows an embodiment of the insertion tool having a flange thereon.

FIG. 24 shows an embodiment of the insertion tool having two flanges.

FIG. 25 shows an embodiment of the insertion tool having a rib thereon.

FIG. 26 shows an embodiment of the insertion tool having two ribs.

FIG. 27 shows an embodiment of the insertion tool having a plurality of longitudinal ribs.

FIG. 28 shows an embodiment of the insertion tool having protrusions.

FIG. 33 shows a vertebral spacer engaging an insertion tool according to the present invention.

FIG. 34 illustrates the system wherein the distal end of a pusher is configured to accept the vertebral spacer.

FIG. 35 illustrates the direction of delivery of the vertebral spacer to an intervertebral space by the insertion tool and the pusher therein.

FIG. 36 illustrates a vertical cross-sectional view of an embodiment of the system for delivery of a vertebral spacer to a patient according to the present invention.

FIG. 37 illustrates a vertical cross-sectional view of another embodiment of the system for delivery of a vertebral spacer to a patient according to the present invention.

FIG. 42 illustrates the placing of an insertion tool into an intervertebral space by using a guiding tool.

FIG. 43 shows the rotation of the insertion tool within the intervertebral space after extraction of the guiding tool.

FIG. 44 illustrates the formation of a vertebral spacer receiving slot by the cutting tool.

FIG. 45 illustrates the delivery of the vertebral spacer into the intervertebral space and the vertebral spacer receiving slot.

DETAILED DESCRIPTION OF THE INVENTION

Figure 3:
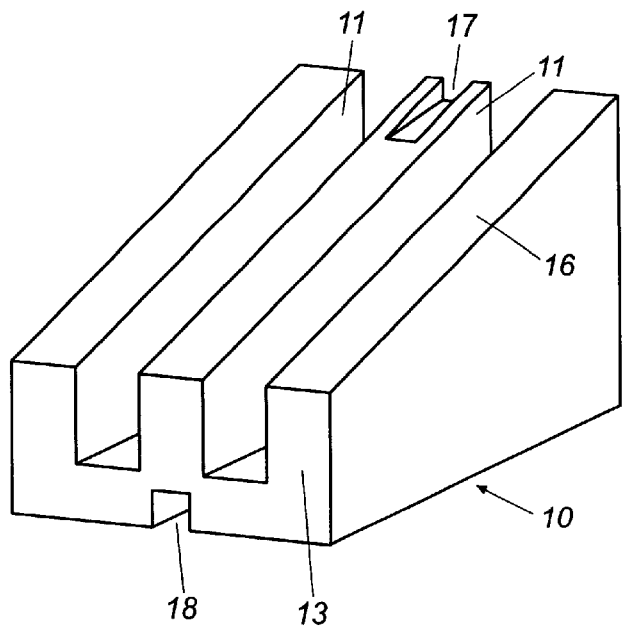
FIG. 3 illustrates another embodiment of the vertebral spacer according to the present invention having two slots extending from the upper surface thereof.
Figure 4:
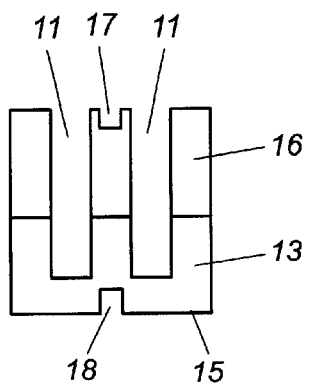
FIG. 4 is an end elevation of the embodiment of the vertebral spacer shown in FIG. 3.
Figure 5:
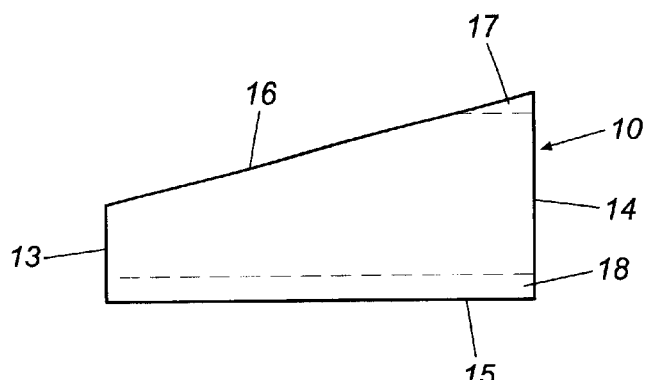
FIG. 5 is a side elevation of the embodiment of the vertebral spacer shown in FIG. 3.
Figure 6:
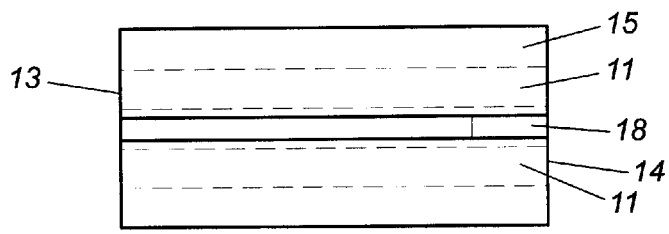
FIG. 6 is a horizontal elevation showing the bottom surface of the embodiment of the vertebral spacer shown in FIG. 3. Positions of the slots relative to the second guiding groove are indicated by dashed lines.

A full and enabling disclosure of the present invention, including the best mode known to the inventor of carrying out the invention, is set forth more particularly in the remainder of the specification, including reference to the accompanying drawings, wherein like reference numerals designate corresponding parts throughout several figures. This description is made for the purpose of illustrating the general principles of the invention and should not be taken in the limiting sense.

One aspect of the present invention is a vertebral spacer for insertion between two adjacent vertebrae 20, thereby maintaining the intervertebral space 23 and preventing compression of the spinal cord therein. Various embodiments of the vertebral spacer 10 in accordance with the present invention are shown in FIGS. 1A–22. The vertebral spacer 10 of the present invention is useful to replace an intervertebral disc 21 that has degenerated due to traumatic injury, vertebral displacement, or disease, such as, for example, autoimmune disease or rheumatoid arthritis or any other pathological condition of the spinal column that may injure or shift the intervertebral disc. The vertebral spacer 10 of the present invention provides support to the vertebrae 20 and maintains separation between vertebrae while also preserving the natural curvature of the spine.

The vertebral spacer 10 of the present invention may have a plurality of surfaces, including a lower surface 15 and an upper surface 16, with the lower surface 15 having an anterior face 13 and a posterior face 14 extending therefrom, as shown in FIG. 1A. The anterior face 13 may be directed towards the inner body cavity of a patient, and the posterior face 14 may be directed towards the dorsal surface of the patient. The vertebral spacer 10 can be configured such that the height of the anterior face 13 is less than the height of the posterior face 14, as is illustrated, for example, in FIG. 1A. The difference in the height of the opposing anterior 13 and posterior 14 faces of the vertebral spacer 10 of the present invention, so that the lower surface 15 and the upper surface 16 are non-parallel, is useful to preserve the natural curvature of the spinal column. The vertebral spacer 10 of the present invention further comprises a first guiding groove 17 in the upper surface 16 or the lower surface 15 of the vertebral spacer 10. The vertebral spacer 10, as contemplated by the present invention, may also have an optional second guiding groove 18 in the upper surface 16 or the lower surface 15 not having the first guiding groove 17 therein.

It is contemplated that the vertebral spacer 10 of the present invention may be of any biocompatible or physiologically inert material or combination of such materials having the mechanical strength capable of maintaining the intervertebral space 23 (FIG. 46) between two adjacent vertebrae 20. Examples of such materials include bone, such as bone sections from the femur, titanium, titanium alloy, stainless steel, chrome cobalt, and polymeric materials such as methyl methacrylate (MMA), urethane, polyacetal and the like. The material of the vertebral spacer 10 may, however, also have a degree of resilience and thereby tolerate a degree of compression. Such materials may include, but are not limited to, polymers such as carbon fiber reinforced polymer such as PEEK (polyetherether ketone), polycarbonate, polypropylene, polyethylene, polyamide and silicone-based polymers.

It is further contemplated that the vertebral spacer 10 of the present invention may comprise a bone core 12 such as a femur and a sheath 35 as shown in FIG. 2.

In one embodiment, the sheath 35 is metallic, such as a tungsten sheath. In another embodiment the sheath comprises a biocompatible polymer. In one embodiment, shown in FIG. 2B, the metallic sheath 35 has angular protrusions 34 thereon.

The vertebral spacer 10 of the present invention may have any conformation that will allow the spacer 10 to be positioned in an intervertebral space 23 between adjacent vertebrae 20 and which will maintain an intervertebral space 23 and the natural curvature of a spinal column when in the desired position. Referring to FIGS. 1A-22, exemplary geometric cross-sections that may be applied to the vertebral spacer 10 of the present invention include, but are not limited to, a rectangular cross-section or a trapezoidal cross-section.

As shown in FIGS. 1B and 2B, the upper surface 16, and optionally the lower surface, of the vertebral spacer 10 can also include at least one protrusion 34 for frictionally engaging a vertebrae 20. An exemplary embodiment of the protrusions 34 of the present invention traversing the upper surface 16 of the vertebral spacer 10 are illustrated in FIG. 1B. In another embodiment of the vertebral spacer 10 of the present invention, as shown in FIG. 2B, the protrusions are located on a metallic sheath 35 encapsulating a bone core 12. The protrusions 34 may have any suitable geometric configuration that will allow the vertebral spacer 10 of the present invention to be secured to adjacent vertebrae, including having a triangular, rounded, or rectangular cross-section and the like, or any combination thereof. The protrusions maybe elongated as shown in FIG. 1B, or any other shape such as square or circular protrusions or irregular non-elongated protrusions.

When the vertebral spacer 10 comprises a section of a femur and wherein the femur medullary cavity 19 connects the anterior face 13 and the posterior face 14 of the vertebral spacer 10, as shown in FIG. 2, the hardening biocompatible composition may be delivered to the portion of the femur medullary cavity 19. With the alternative embodiments of the vertebral spacer 10 having at least one slot 11 extending from the upper surface 16 or lower surface 15, the hardening biocompatible composition may be delivered to the slots 11 thereof. One embodiment of the method of the present invention, therefore, further comprises the step of delivering a hardening biocompatible composition to the vertebral spacer 10. The hardening biocompatible composition may be used, for example, to bond the vertebral spacer 10 to an adjacent vertebra or be an osteogenic composition to promote bone growth from the adjacent vertebrae into the vertebral spacer 10. The hardening biocompatible composition may be, for example, an organic polymer, a mineral composition such as a hydroxyapatite-based compositions, methyl methacrylate or a combination thereof. A hydroxyapatite-based composition is especially useful in the context of the present invention for promoting osteocyte growth and bone deposition.

Figure 46:
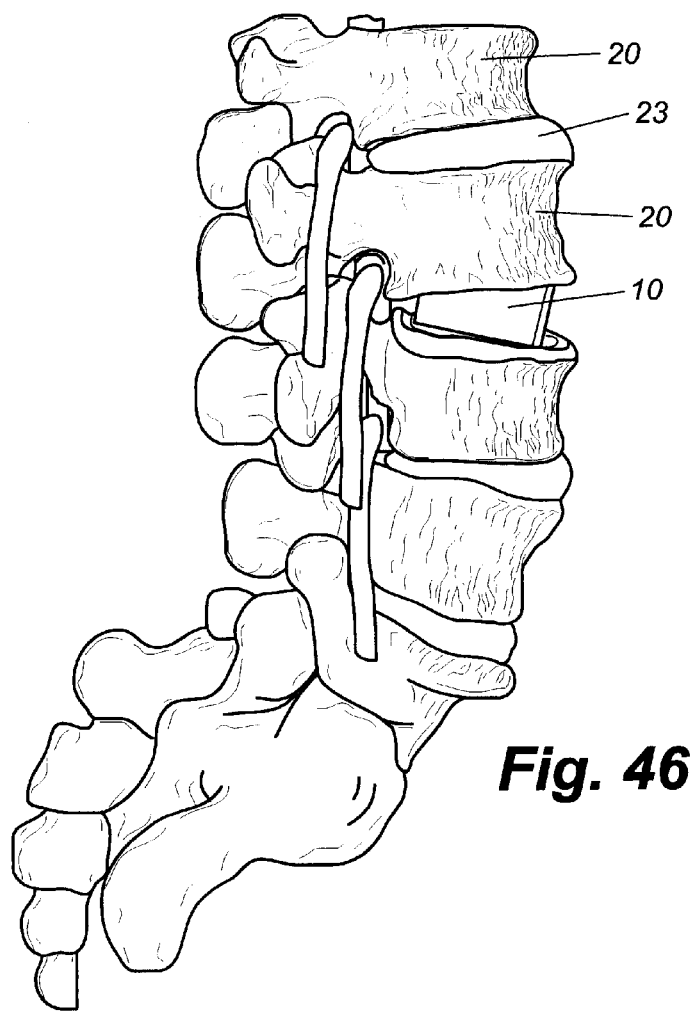
FIG. 46 is a perspective view showing an embodiment of the vertebral spacer according to the present invention in situ in an intervertebral space of a patient.

The direction of insertion of the vertebral spacer 10 by the methods of the present invention can be selected by the surgeon according to the needs of the patient. The anterior face 13 of the vertebral spacer 10, for example, may be positioned relative to the spine to maintain a desired curvature thereof, as shown in FIG. 46. The vertebral spacer 10 may be inserted posteriorly as shown, for example in FIG. 46, anteriorly, or laterally, relative to the spinal column. Once inserted into a desired position in the intervertebral space 23, as shown in FIG. 46, the lower surface 15 and the upper surface 16 of the vertebral spacer 10 are substantially contacting the adjacent vertebrae 20. For example, the lower surface 15 of the vertebral spacer 10 may contact the lower vertebra 20, and the upper surface 16 may support the adjacent upper vertebra 20. Optional protrusions 34 extending from the upper surface 16 as shown, for example, in FIG. 1B, and/or the lower surface 15 can increase the frictional resistance between the vertebral spacer 10 and the adjacent vertebrae 20. As shown in FIG. 46, the vertebral spacer 10 of the present invention can support adjacent vertebrae 20 after the partial or total surgical removal of an intervertebral disc 21, thereby preventing collapse and/or compression of the spine in this region that might otherwise lead to severe neurological damage.

In another embodiment of the vertebral spacer 10 of the present invention, at least one slot 11 may be formed in the upper surface 16 and extend towards, but not connecting with, the opposing lower surface 15, as shown in FIGS. 3–6. Alternatively, the at least one slot 11 may be formed in the lower surface 15 and extend towards the upper surface 16.

Figure 7:
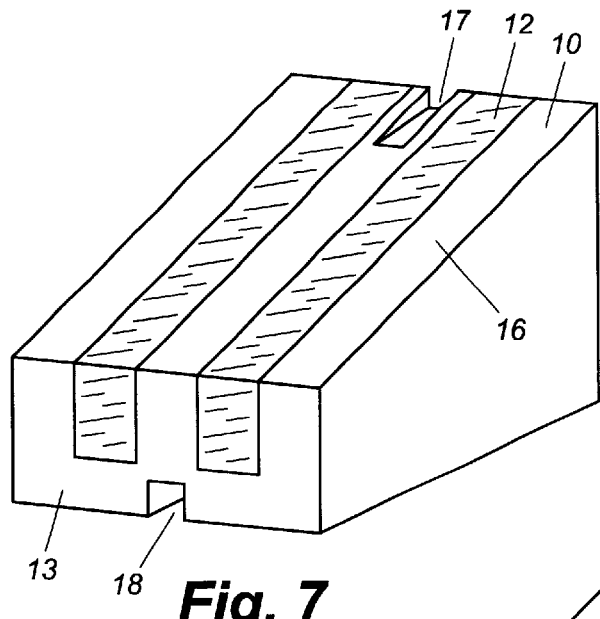
FIG. 7 illustrates another embodiment of the vertebral spacer according to the present invention wherein slots extending from the upper surface thereof accommodate bone material therein.

In still another embodiment of the vertebral spacer 10 of the present invention, the at least one slot 11 has a bone core 12 disposed therein, as shown in FIG. 7. Alternatively, a hardening biocompatible composition may be deposited in the at least one slot 11, wherein the hardening biocompatible composition generally comprises an osteogenic compound such as, for example, hydroxyapatite.

Figure 8:
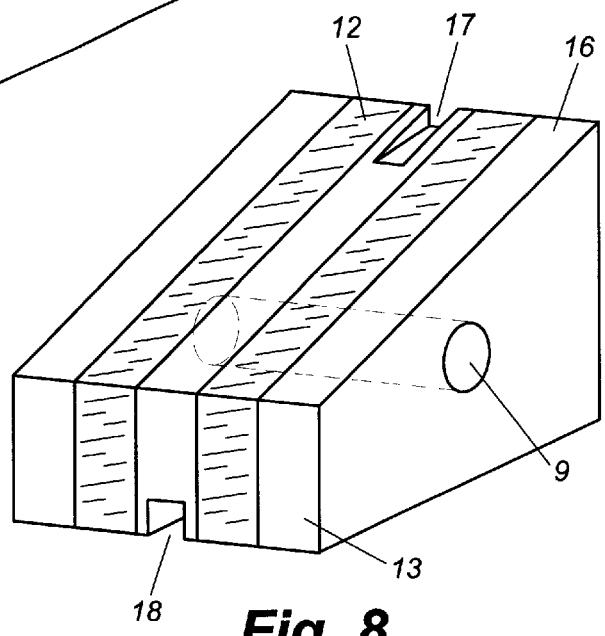
FIG. 8 illustrates another embodiment of the vertebral spacer comprising alternate layers of bone, a biocompatible material, and a linking pin.
Figure 9:
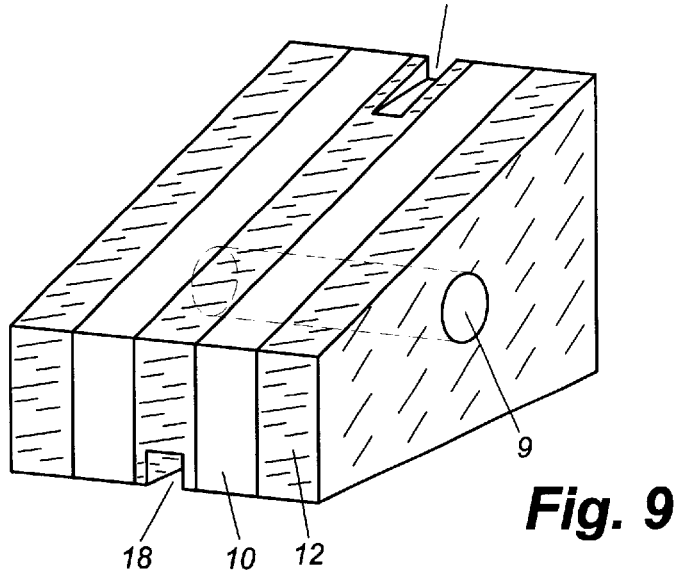
FIG. 9 illustrates another embodiment of a layered vertebral spacer according to the present invention wherein the outermost layers are bone.
Figure 17:
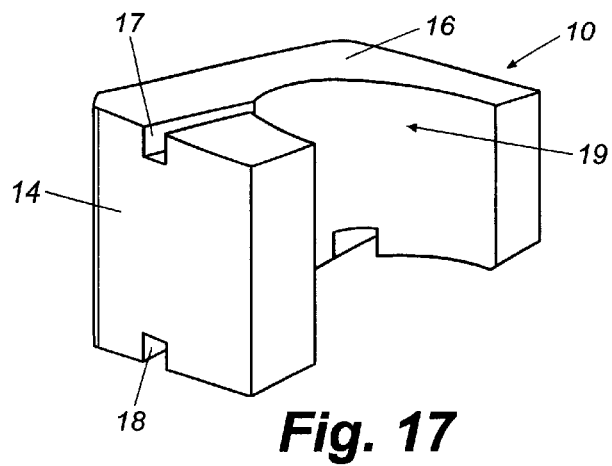
FIG. 17 is a perspective view of a vertebral spacer according to the present invention excised from a femur.
Figure 18:
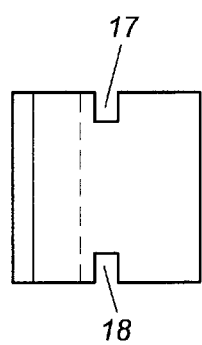
FIG. 18 is an end elevation of the vertebral spacer illustrated in FIG. 17.
Figure 19:
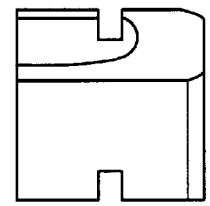
FIG. 19 is a perspective view of another vertebral spacer according to the present invention cut from the same section of femur as the spacer in FIG. 17.
Figure 20:
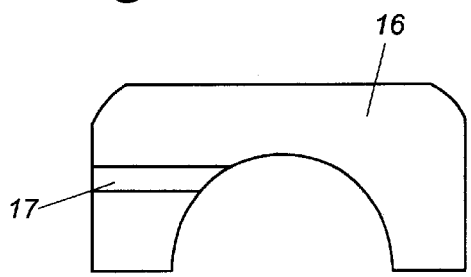
FIG. 20 shows a top elevation of a vertebral spacer according to the present invention cut from a femur section.
Figure 21:
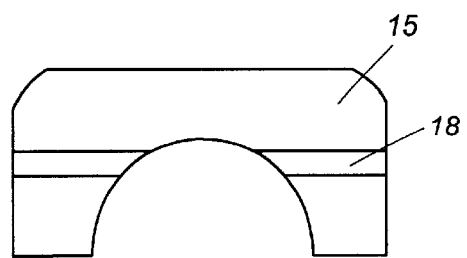
FIG. 21 shows a bottom elevation of a vertebral spacer according to the present invention cut from a femur section.

In another embodiment of the vertebral spacer 10 of the present invention, shown in FIGS. 8 and 9, the spacer 10 comprises a plurality of layers, wherein at least one layer is a bone core 12. The plurality of layers may be bonded by any suitable method such as an adhesive, screws, bolts, a linking pin, or the like, and which will hold the layers immobile relative to each other. In one embodiment of the vertebral spacer 10 of the present invention, as shown in FIG. 9, may be bonded by at least one pin 9. In another embodiment of the vertebral spacer 10, the plurality of layers may be bonded by two pins positioned to prevent movement of the layers relative to each other. The bonding method will not impede installation of the vertebral spacer 10 into the intervertebral space 23 (FIG. 46) of a patient. The alternate layers may have bone cores 12 as inner layers as shown in FIGS. 7 and 8, or as the outermost layers of the vertebral spacer 10, as shown in FIG. 9.

Referring now to FIGS. 10–22, in another embodiment of the vertebral spacer 10 of the present invention, the vertebral spacer 10 is formed from a femoral section 24 taken from the shaft 22 of a femur, as shown in FIG. 10. The femoral section 24, having a central femur medullary cavity 19 therein, maybe trimmed as shown in FIGS. 11, 12, 15 and 16 to yield at least one vertebral spacer 10. Each vertebral spacer 10 obtained from a femur shaft 22 will have at least a portion of the femur medullary cavity 19 connecting the upper 16 and lower 15 surfaces of the vertebral spacer 10. The indented portion of the femur medullary cavity 19 is useful to partially surround a spinal cord when the vertebral spacer 10 is positioned within an intervertebral space, thereby allowing the vertebral spacer 10 to be positioned closer to the spinal cord than would be possible if the cavity 19 were not present. The vertebral spacer 10 of the present invention, when excised from a femur shaft 22 (FIG. 10) also has a first guiding groove 17, and optionally, a second guiding groove 18, in the upper 16 and/or lower 15 surfaces respectively of the vertebral spacer 10, as shown in FIGS. 11–22.

Figure 22:
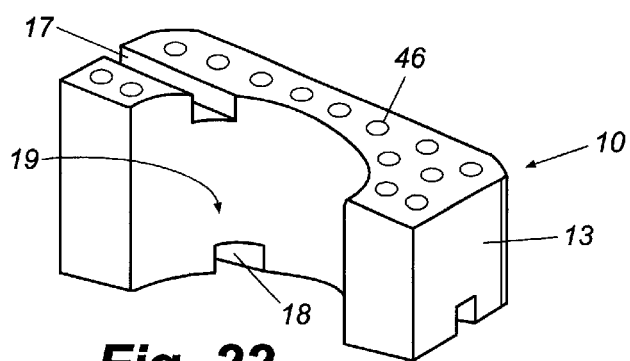
FIG. 22 illustrates a perspective view of a vertebral spacer according to the present invention cut from a femur section and having a plurality of bores therein.
Figure 23:
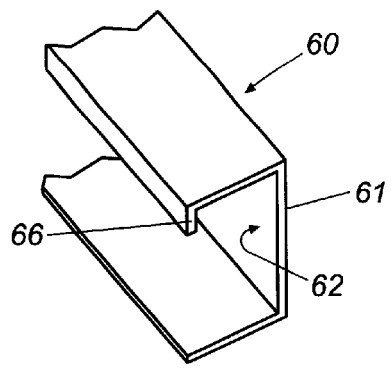
FIGS. 23–28 illustrate perspective cross-sectional views of embodiments of the insertion tool according to the present invention.
Figure 24:
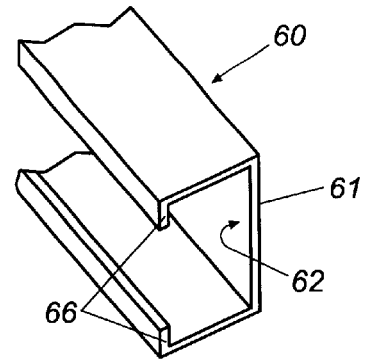

Referring now to FIG. 22, the vertebral spacer 10 of the present invention may further include a bore 46, or a plurality of bores 46, extending from the upper surface 16 and/or the lower surface 15 of the vertebral spacer 10. Bony or other tissue growth from adjacent vertebrae that extends into the bore 46, or plurality of bores 46, of the vertebral spacer 10 of the present invention may bond the vertebrae and the vertebral spacer 10. The bony growth will, therefore, effectively fuse the adjacent vertebrae. It is further contemplated that a tissue growth factor or an osteogenic material may be inserted into the bores to increase the bony growth and, therefore, the rate of this fusion. Suitable growth factors include, but are not limited to, growth hormones, steroids, tissue growth factors and the like.

Another aspect of the present invention is a system for delivering a vertebral spacer 10 to the spinal column of a patient, generally illustrated in FIGS. 24–41. The system for delivering the vertebral spacer comprises (a) an insertion tool 60 for delivering the vertebral spacer 10 to the spinal column of a patient, wherein the insertion tool 60 has a channel 61 and an inner surface 62 as shown in FIGS. 24–28; (b) an optional guiding tool 80; (c) a pusher 63 (as in FIGS. 31–37) having a distal end 65 slideably disposable in the channel 61 of the insertion tool 60; (d) a vertebral spacer 10 slideably disposable in the channel 61 of the insertion tool 60; and (e) a cutting tool 70 (FIGS. 38–41) having a shaft 72 with a distal end 74 and a proximal end 75, and a cutting head 71 secured to the distal end 74 of the shaft 72.

The channel 61 of the insertion tool 60 of the system of the present invention generally is configured to slideably accept any of the various vertebral spacers 10, according to the present invention, a pusher 63 and/or a cutting tool 70. The insertion tool 60 further comprises at least one spacer guide 66 for slideably engaging with a first guiding groove 17 or a second guiding groove 18 of a vertebral spacer 10.

According to at least one embodiment of the invention, as clearly depicted in FIGS. 23–28, the channel 61 of the insertion tool 60 is an open channel (that is, being open along its length); and according to at least one embodiment of the invention, as clearly depicted in FIGS. 23–28, the channel 61 of the insertion tool 60 is a half-open channel (that is, being open along its length and with the channel displaying in end-view cross-section a perimeter wall that encompasses greater than or equal to 180 degrees of a closed-walled object). According to at least one embodiment of (the invention, as depicted in FIGS. 23–28, the channel 61 of the insertion tool 60 is an elongated rectangular channel (that is, an elongated channel displaying in end-view cross-section an interior wall defining a rectangle), and the rectangular channel may also be half-open.

Figure 25:
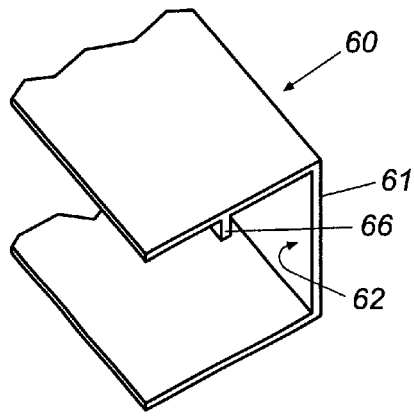
Figure 26:
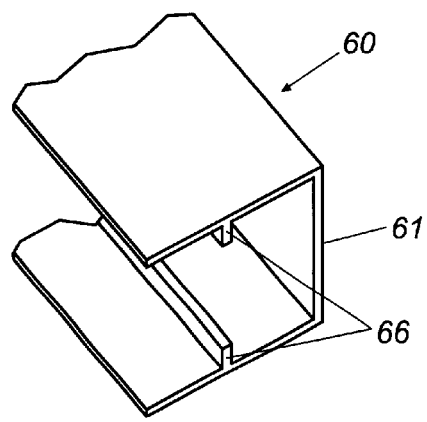

In still another embodiment of the insertion tool 60 of the present invention as shown in FIGS. 25 and 26, the spacer guide 66 is formed as one or more ribs longitudinally disposed on an inner surface 62 of the channel 61.

Figure 27:
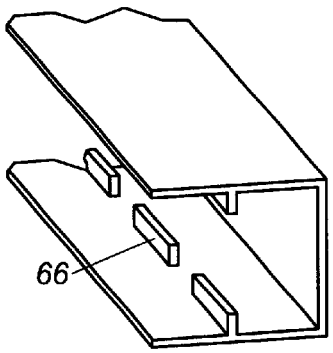
Figure 28:
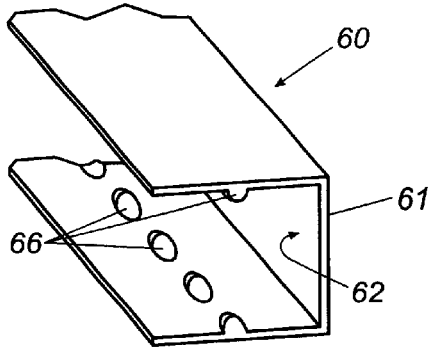

In other embodiments of the insertion tool 60 of the present invention, the spacer guide 66 may be formed by at least one segmented longitudinal rib disposed on the inner surface 62 of the channel 61, as shown in FIG. 27, or a linear series of spaced protrusions, also disposed on the inner surface 62 of the channel 61, as shown in FIG. 28. It is to be understood, however, that any configuration of spacer guides 66 may be used by the insertion tool 60 that will allow a vertebral spacer to be slideably engaged with the insertion tool 60 and not resist insertion of the vertebral spacer into the spinal column of a patient.

Figure 29:
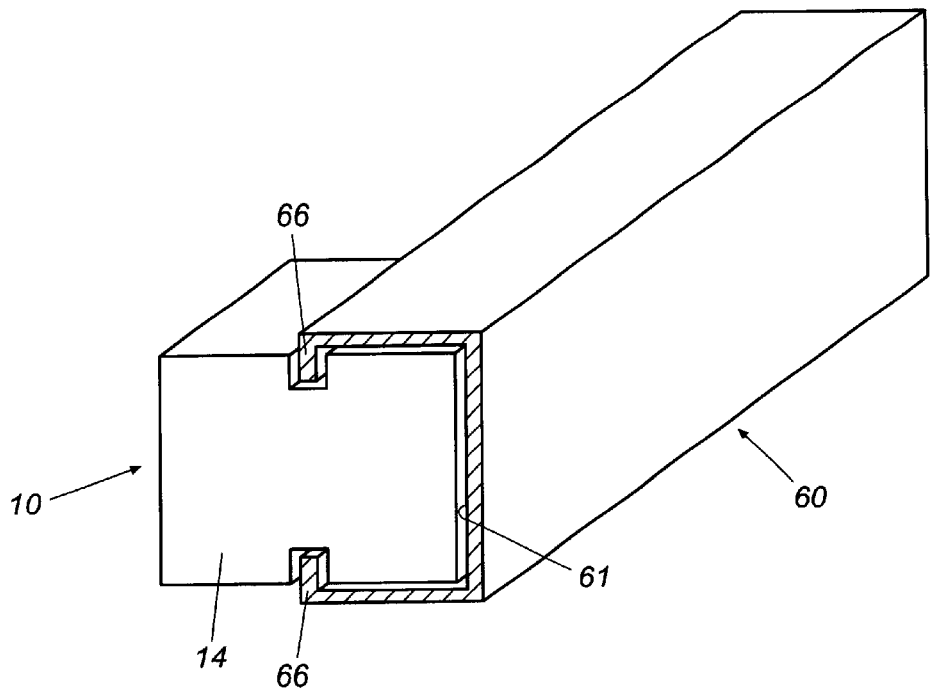
FIG. 29 illustrates a perspective view of the system for delivering a vertebral spacer to a patient according to the present invention wherein the vertebral spacer engages two flanges on the insertion tool.
Figure 30:
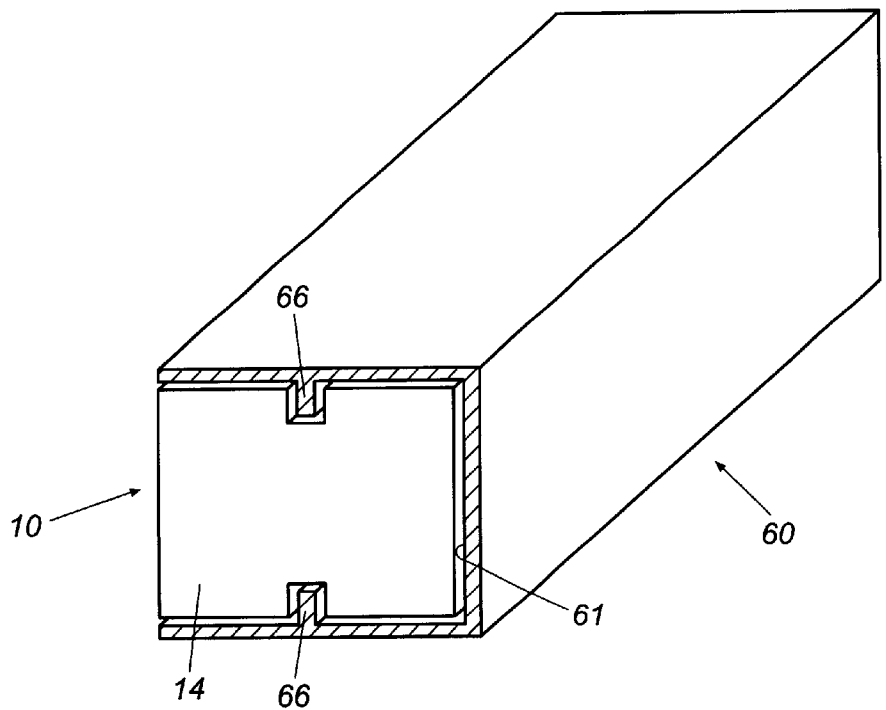
FIG. 30 illustrates a perspective view of the system for delivering a vertebral spacer to a patient according to the present invention wherein the vertebral spacer engages two ribs on the insertion tool.
Figure 31:
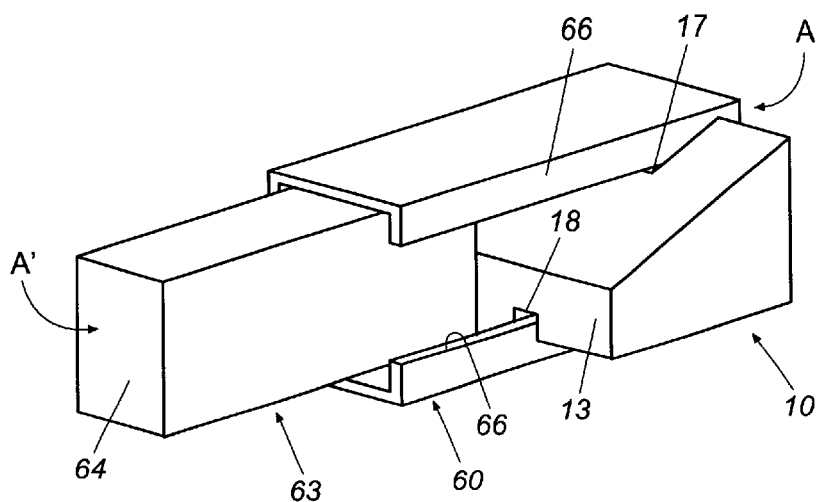
FIG. 31 illustrates a perspective view of an embodiment of the system for delivering a vertebral spacer to a patient wherein the insertion tool has two flanges.

As shown in FIGS. 29–35, the spacer guide 66, or a plurality of guides 66, may slideably engage the first 17 and optional second 18 guiding groove with at least a portion of the vertebral spacer 10 positioned externally to the channel 61, as illustrated in FIGS. 29 and 31.

Figure 42:
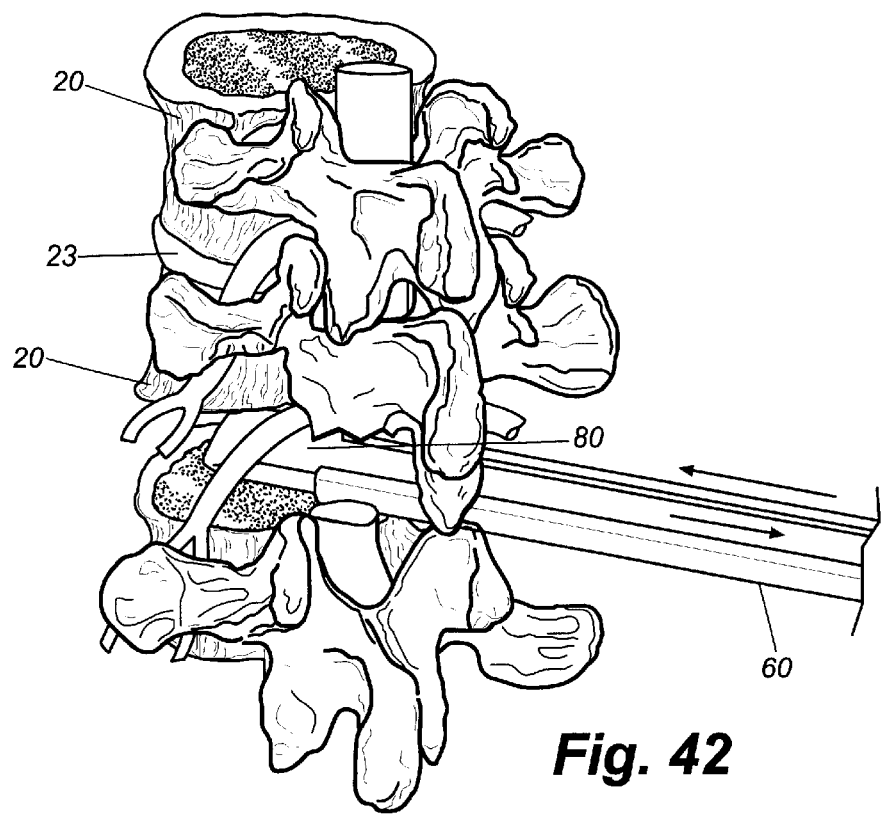
FIGS. 42–45 illustrate the delivery of a vertebral spacer to an intervertebral space according to the methods of the present invention.
Figure 43:
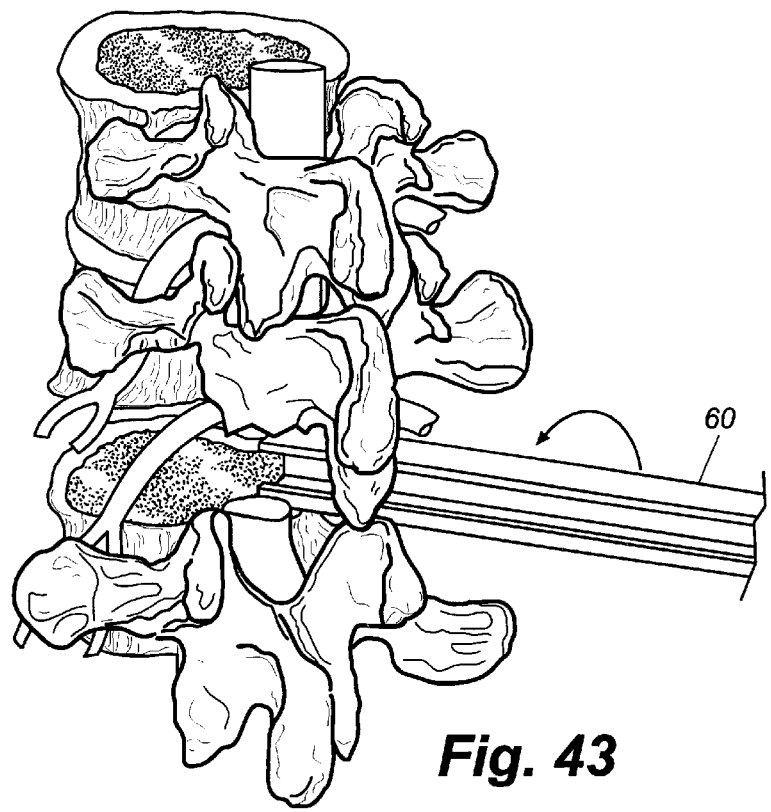

The present invention also provides an optional guide tool 80 that can be slideably disposed in the channel 61 of the insertion tool 60. The elongated optional guide tool can be inserted into an intervertebral space 23 as indicated in FIGS. 42–43, to a position selected by a surgeon for guiding the insertion tool 60 to the same selected position.

As shown in FIGS. 31–32, 34–37, and 45, the system for delivery of a vertebral spacer 10 to the spinal column of a patient further comprises a pusher 63 having a distal end 65 for contacting a vertebral spacer 10 disposed in the channel 61. It is contemplated that the pusher 63 can be slideably engaged in the channel 61 of the insertion tool 60 and is suitable for enabling a surgeon to push a vertebral spacer 10 along the channel 61, out of the insertion tool 60 and into an intervertebral space 23.

Figure 32:
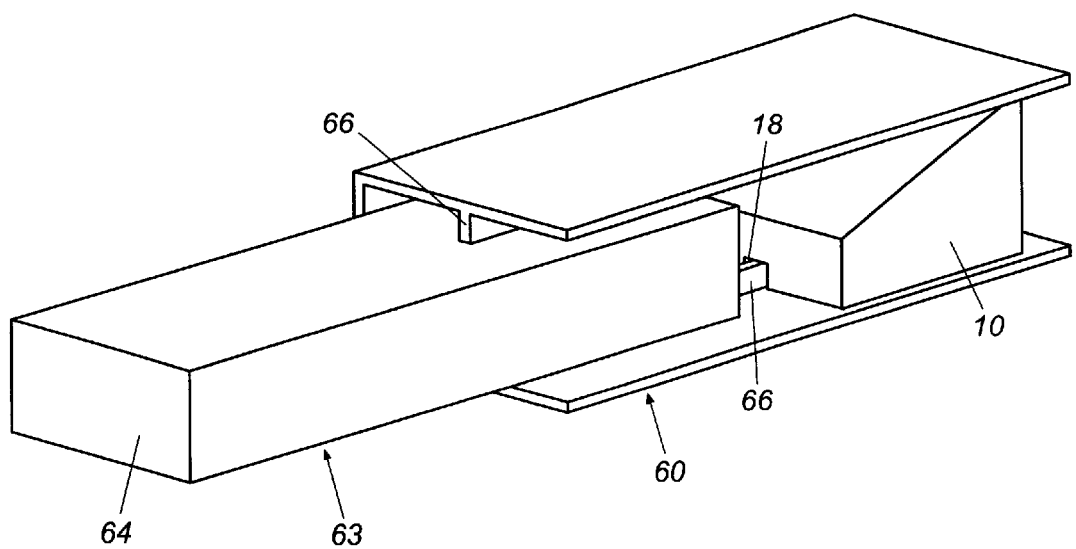
FIG. 32 illustrates a perspective view of an embodiment of the system for delivering a vertebral spacer to a patient wherein the insertion tool has two ribs.
Figure 33:
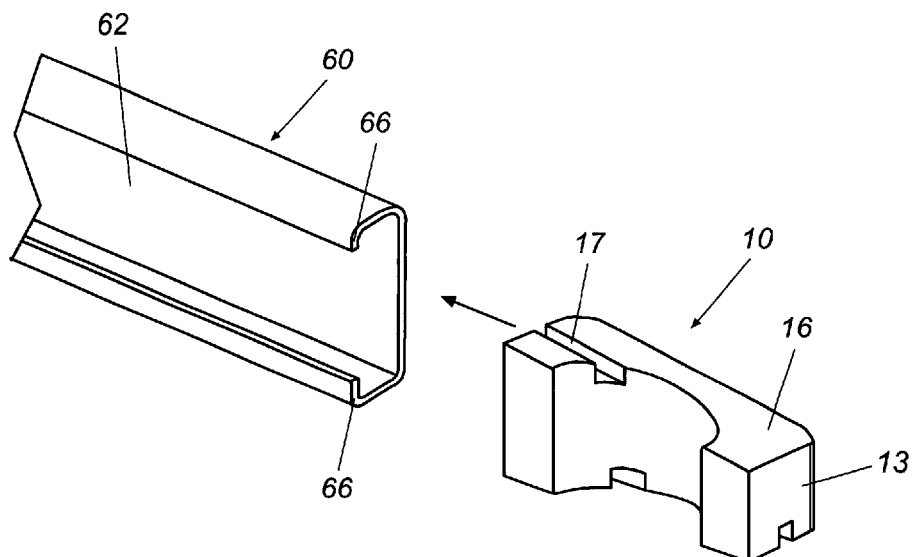
FIGS. 33–35 illustrate the assembly of an embodiment of the system for delivering a vertebral spacer to a patient.
Figure 34:
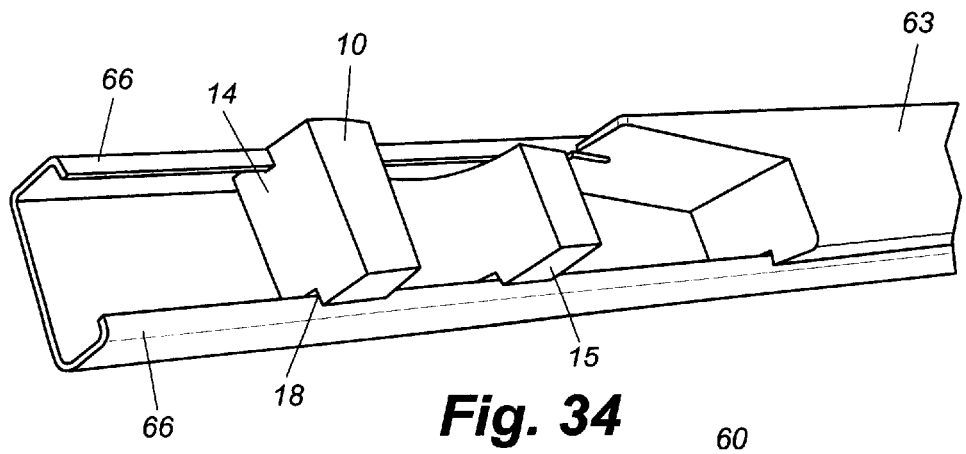
Figure 35:
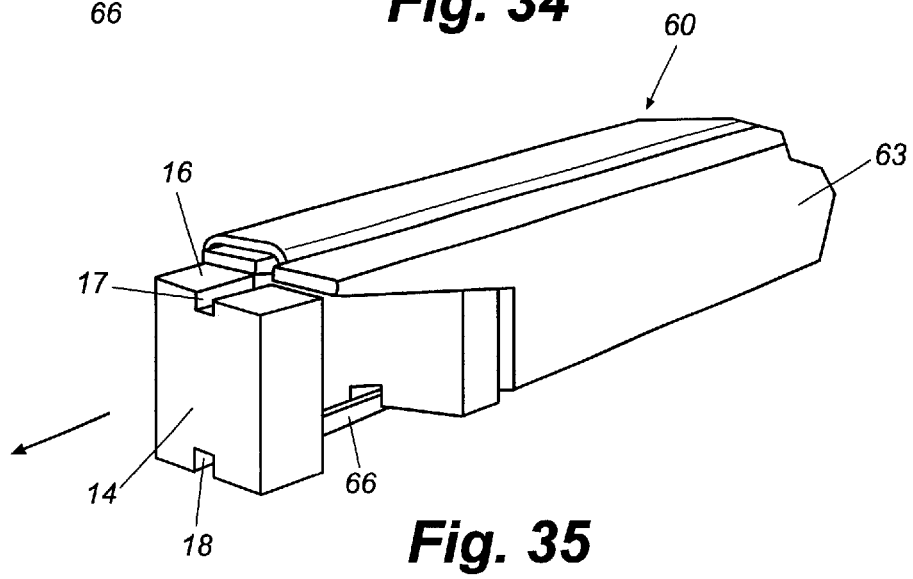
Figure 38:
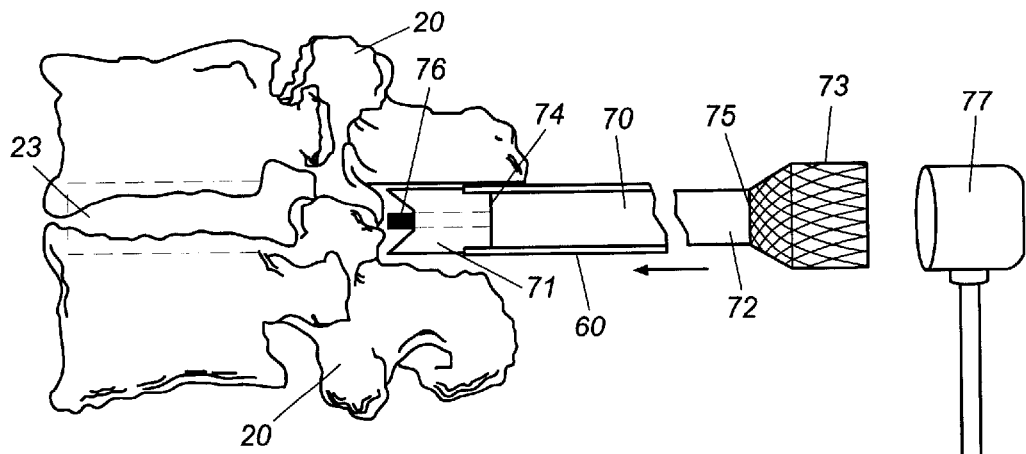
FIG. 38 illustrates the cutting of a vertebral spacer receiving slot by an embodiment of the cutting tool according to the present invention.

In one embodiment of the pusher of the present invention as illustrated in FIGS. 31 and 32, the distal end 65 may be substantially parallel to the posterior face 14 of the vertebral spacer 10. This orientation is especially useful for inserting a vertebral spacer 10 of the present invention in the lumbar region of a spinal column. It is to be understood, however, that the vertebral spacer 10 may be inserted in the insertion tool 60 in the opposite orientation for insertion in another region of the spine where reverse curvature to that of the lumbar region is to be maintained. In other embodiments of the present invention such as shown, for example, in FIGS. 34, 35 and 37, the configuration of the distal end 65 of the pusher 63 may be defined by the anterior face 13 and the upper surface 16 of the vertebral spacer 10.

As illustrated in FIGS. 38–41, the system for the delivery of a vertebral spacer 10 to the spinal column of a patient further provides a cutting tool 70 suitable for cutting a vertebral spacer receiving slot 78 into a vertebra 20. The cutting tool 70 of the present invention has a shaft 72 with a distal end 74 and a proximal end 75. A cutting head 71 is connected to the distal end 74 of the shaft 72 of the cutting tool 70. In one embodiment of the cutting tool 70 of the present invention, a striking head 73 is disposed on the proximal end 75 of the shaft 72.

Figure 39:
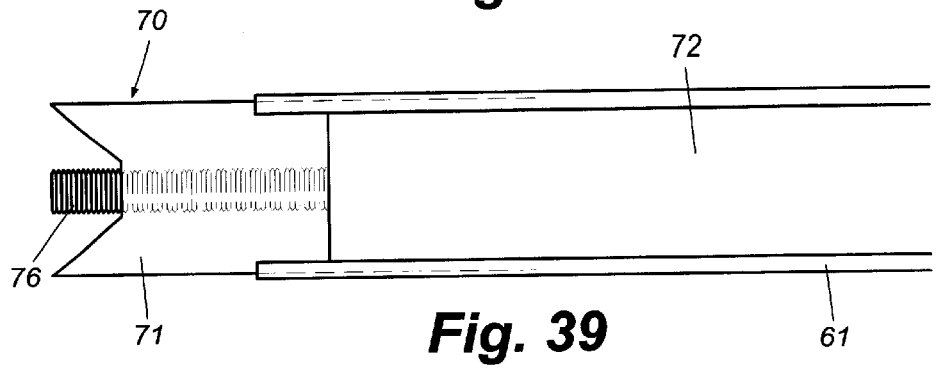
FIG. 39 is a side-elevation of an embodiment of the cutting tool and insertion tool according to the present invention.
Figure 40:
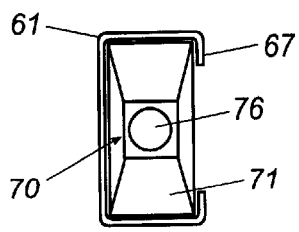
FIG. 40 illustrates an end-elevation of an embodiment of the cutting tool according to the present invention.
Figure 41:
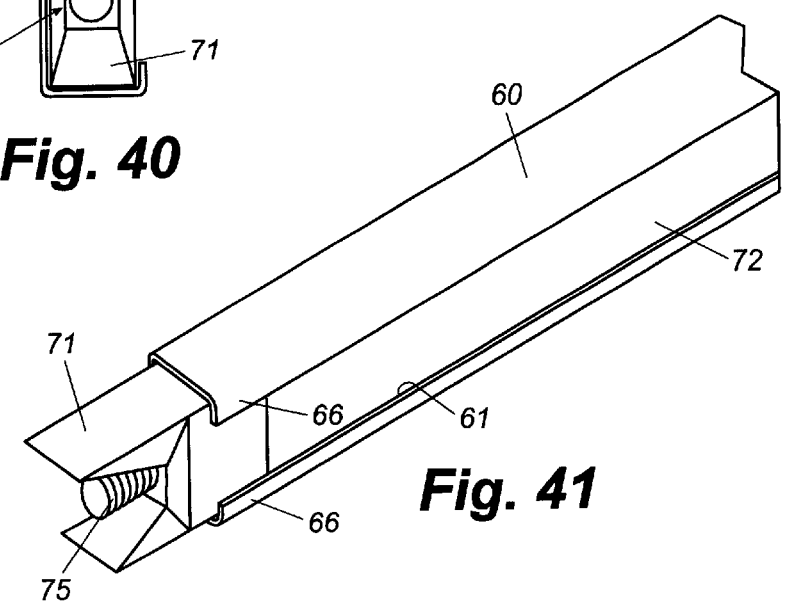
FIG. 41 is a perspective view of an embodiment of the cutting tool and the insertion tool according to the present invention.

The cutting head 71 of the cutting tool 70 may be an integral configuration of the distal end 74 of the shaft 72, or connected to the distal end 74 of the shaft 72. In one embodiment of the cutting tool 70 of the present invention, the cutting head 71 is connected to the shaft by an attachment member 76 which may be, for example, a threaded attachment member 76, as shown in FIGS. 39 and 40. The cutting head 71 will be capable of being slideably disposed within the channel 61 of the insertion tool 60 providing that the pusher 63 and the vertebral spacer 10 are not disposed therein.

Another aspect of the present invention is a method for delivering a vertebral spacer 10 to a patient using the system of the present invention comprising the insertion tool 60, an optional guide tool 80, the vertebral spacer 10, the pusher 63 and the cutting tool 70. Such a method is generally illustrated in FIGS. 42–45 and comprises the steps of inserting the insertion tool 60 into an intervertebral space 23 of the spinal column of a patient (FIG. 42), rotating the insertion tool 60 in the intervertebral space 23 (FIG. 43), cutting a vertebral spacer receiving slot 78 (FIG. 44), and engaging the first guiding groove 17, and optionally a second guiding groove 18, of a vertebral spacer 10 with a space guide 66 of the insertion tool 60. The vertebral spacer 10 is pushed into the intervertebral space 23 by slideably disposing a pusher 63 into the channel 61 of the insertion tool 60, and advancing the pusher 63 (FIG. 45). The pusher 63 and the insertion tool 60 are then removed from the patient.

The insertion tool 60 further optionally may be directed into the selected position within the intervertebral space 23 by the guide tool 80 that may be inserted by the surgeon into the intervertebral space 23. The method of the present invention, therefore, further comprises the optional step of inserting a guiding tool 80 into an intervertebral space 23.

The insertion tool 60 may then be slid along the guide tool 80 until the insertion tool 60 is at the selected position for insertion of a vertebral spacer 10 in the intervertebral space 23. The guide tool 80 is then removed from the channel 61 of the insertion tool 60, as shown in FIG. 42, leaving the insertion tool 60 inserted between adjacent vertebrae 20. Alternatively, the guide tool 80 may remain in the insertion tool 60 while the insertion tool 60 is rotated in the intervertebral space 23, thereby providing torsional strength to the insertion tool 60. The insertion tool 60 may be inserted into the intervertebral space 23 with the channel 61 facing a vertebra 20, as shown in FIG. 42. The insertion tool 60 may then be rotated so that the open channel 61 of the tool 60 is not facing a vertebra 20, as shown in FIG. 43.

Figure 44:
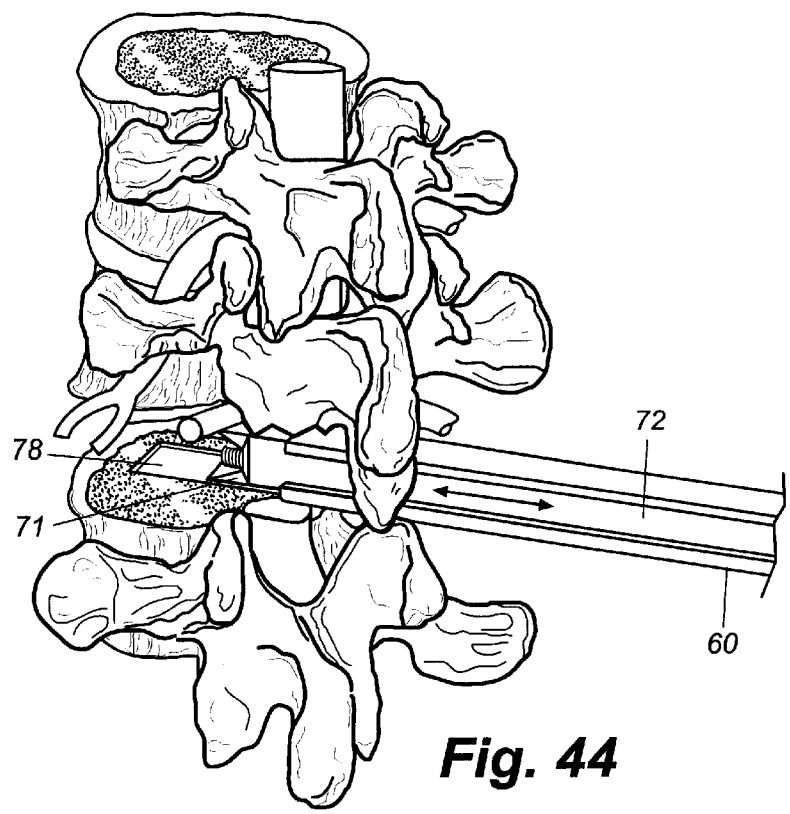
Figure 45:
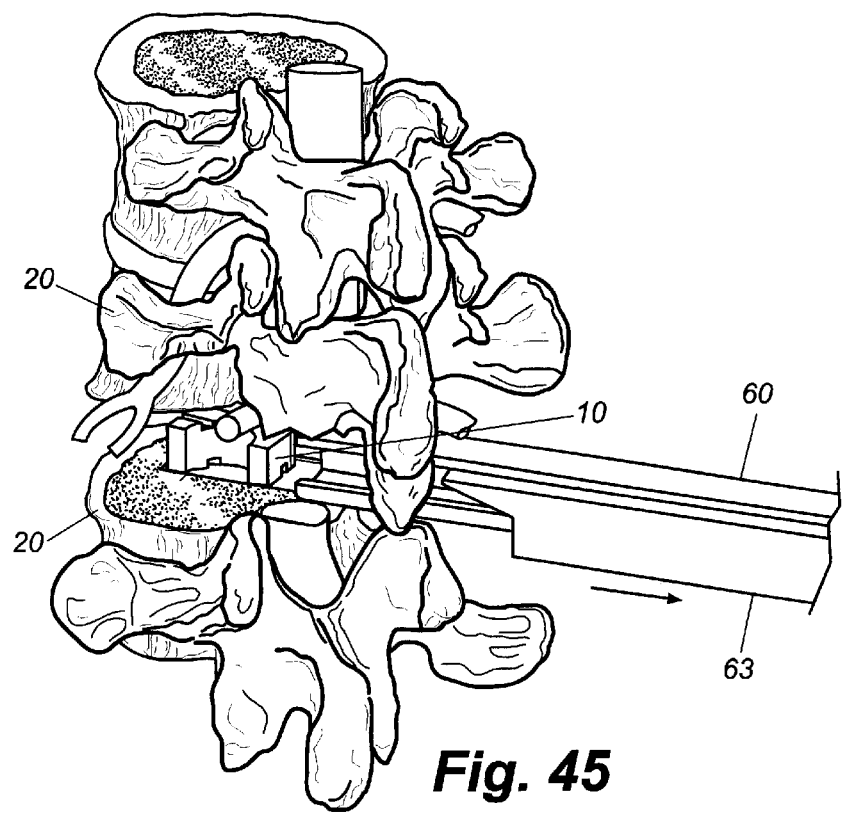

As shown in FIG. 44, the cutting tool 70 is optionally slid along the channel 61 of the insertion tool 60 to engage a vertebra 20 and to chisel a vertebral space receiving slot 78 in the vertebrae 20. Alternatively, two vertebral spacer receiving slots 78 may be cut in opposing faces of adjacent vertebrae 20. The striking head 73 of the cutting tool 70 may be struck with a striking tool 77 to increase the cutting action of the cutting head 71.

As shown in FIG. 45, the cutting tool 70 is removed from the patient by slideably withdrawing the cutting tool 70 back through the channel 61 of the insertion tool 60. A vertebral spacer 10 according to the present invention may then be slideably engaged with the insertion tool 60, wherein at least one space guide 66 on the insertion tool 60 engages with a first guiding groove 17 and optionally a second guiding groove 18 of the vertebral spacer 10. The pusher 63 may then be slideably engaged with the channel 61 and contacted with the vertebral spacer 10. The pusher 63 is advanced along the channel 61 of the insertion tool 60 thereby pushing the vertebral spacer 10 into the vertebral spacer receiving slot 78 or receiving slots 78 in the adjacent vertebrae 20. It is also contemplated, however, that a vertebral spacer receiving slot 80 may not be cut in the adjacent vertebrae 20 and that the inserted vertebral spacer 10 may optionally contact the uncut surface of the vertebrae 20.

Figure 47:
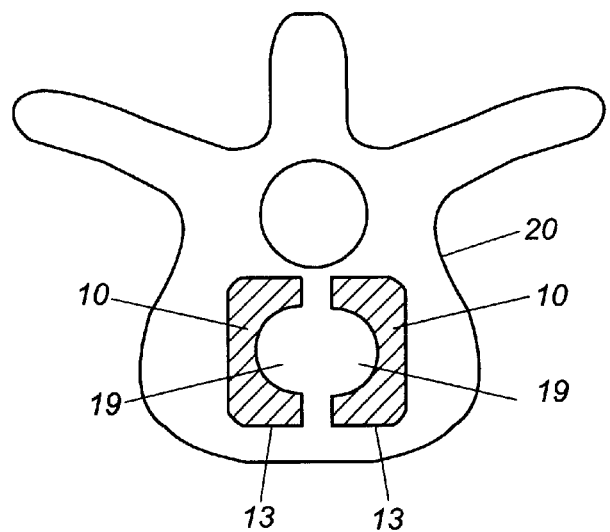
FIG. 47 is an overhead view showing two vertebral spacers formed from a femur on a vertebral surface.

It is to be understood that the methods of the present invention for the delivery of a vertebral spacer 10 to an intervertebral space 23 may also be used to deliver two vertebral spacers 10, as shown in FIG. 47, it is further understood that a hardening biocompatible composition may be delivered between the vertebral spacers, thereby forming a larger effective spacer and optionally promoting bone growth to secure the vertebral spacers 10 to the vertebrae.

Yet another aspect of the present invention is a kit for delivering a vertebral spacer to the spinal column of a patient, comprising an insertion tool for delivering a vertebral spacer to the spinal column of a patient and having a channel having an inner surface, a pusher having a distal end is slideably disposable in the channel of the insertion tool, a vertebral spacer slideably disposable in the channel of the insertion tool, a cutting tool having a shaft with a distal end and a proximal end, and a cutting head secured to the distal end of the shaft, wherein the cutting tool is slideably disposable in the insertion tool providing that the pusher and the vertebral spacer are not disposed therein. Instructions for the use of the system and its various components to deliver a vertebral spacer to the spinal column of a patient also generally are included or provided.

The kit of the present invention further can include an optional guiding tool configured to slideably engage the channel of the insertion device, and instructions for the operation thereof.

With respect to the above description, it is to be realized that the optimum dimensional relationships for the parts of the invention, to include variations in size, materials, shape, form, function and manner of operation, assembly, and use, are deemed readily apparent and obvious to one skilled in the art, and all equivalent relationships to those illustrated in the drawing and described in the specification are intended to be encompassed by the present invention. Further, the various components of the embodiments of the invention may be interchanged to produce further embodiments and these further embodiments are intended to be encompassed by the present invention.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A system for delivering a vertebral spacer to the spinal column of a patient, comprising:
   (a) an insertion tool for delivering a vertebral spacer to the spinal column of a patient, comprising an open channel having an inner surface;
   (b) a pusher, having a distal end, slideably disposable in the open channel of the insertion tool;
   (c) a vertebral spacer slideably disposable in the open channel of the insertion tool; and
   (d) a cutting tool having a shaft with a distal end and a proximal end, and a cutting head secured to the distal end of the shall, wherein the cutting tool is slideably disposable in the insertion tool providing that the pusher and the vertebral spacer are not disposed therein.

2. The system of claim 1, further comprising a guiding tool configured to slideably engage the open channel of the insertion tool.

3. The system of claim 1, wherein the distal end of the pusher is configured to receive the vertebral spacer.

4. The system of claim 1, wherein the cutting tool further comprises an attachment member for securing the cutting head to the distal end of the shaft.

5. The system of claim 1, further comprising instructions for the use of the system to deliver a vertebral spacer to the spinal column of a patient.

6. The system of claim 1, further comprising a guiding tool configured to slideably engage the channel of the insertion device and instructions for the operation thereof.

7. The system of claim 1, wherein the insertion tool has a spacer guide slideably engaging the vertebral spacer.

8. The system of claim 7, wherein the spacer guide is at least one flange disposed on the channel of the insertion tool.

9. The system of claim 7, wherein the spacer guide is at least one rib longitudinally disposed on the inner surface of the channel of the insertion tool.

10. The system of claim 7, wherein the spacer guide is a protrusion on the inner surface of the channel of the insertion device.

11. The system of claim 7, wherein the spacer guide comprises a plurality of protrusions on the inner surface of the channel of the insertion device.

12. The system of claim 7, wherein the channel is a rectangular channel.

13. The system of claim 1, wherein said channel of said insertion tool defines a half-open channel.

14. The system of claim 13, wherein the insertion tool has a spacer guide slideably engaging the vertebral spacer.

15. The system of claim 14, wherein the spacer guide is at least one flange disposed on the half-open channel of the insertion tool.

16. The system of claim 14, wherein the spacer guide is at least one rib longitudinally disposed on the half-open surface of the half-open channel of the insertion tool.

17. The system of claim 14, wherein the spacer guide is a protrusion on the inner surface of the half-open channel of the insertion device.

18. The system of claim 14, wherein the spacer guide comprises a plurality of protrusions on the inner surface of the half-open channel of the insertion device.

19. The system of claim 1, wherein the channel is a rectangular channel.

20. The system of claim 19, wherein said channel of said insertion tool defines a half-open channel.

21. The system of claim 20, wherein the spacer guide is at least one flange disposed on the rectangular half-open of the insertion tool.

22. The system of claim 20, wherein the spacer guide is at least one rib longitudinally disposed on the inner surface of the rectangular half open of the insertion tool.

23. The system of claim 20, wherein the spacer guide is a protrusion on the inner surface of the rectangular half-open channel of the insertion device.

24. The system of claim 20, wherein the space guide comprises a plurality of protrusions on the inner surface of the rectangular half-open channel of the insertion device.

25. A system for delivering a vertebral spacer to the spinal column of a patient, comprising:
   (a) an insertion tool for delivering a vertebral spacer to the spinal column of a patient, comprising a channel having an inner surface;
   (b) a pusher having a distal end slideably disposable in the channel of the insertion tool;
   (c) a vertebral spacer slideably disposable in the channel of the insertion tool;
   (d) a cutting tool having a shaft with a distal end and a proximal end, and a cutting head secured to the distal end of the shaft, wherein the cutting tool is slideably disposable in the insertion tool providing that the pusher and the vertebral spacer are not disposed therein; and
wherein the insertion tool has a spacer guide slideably engaging the vertebral spacer.

26. The system of claim 25, wherein the spacer guide is at least one flange disposed on the channel of the insertion tool.

27. The system of claim 25, wherein the spacer guide is at least one rib longitudinally disposed on the inner surface of the channel of the insertion tool.

28. The system of claim 25, wherein the spacer guide is a protrusion on the inner surface of the channel of the insertion device.

29. The system of claim 25, wherein the spacer guide comprises a plurality of protrusions on the inner surface of the channel of the insertion device.

30. The system of claim 25, wherein the channel is a rectangular channel.

31. The system of claim 30, wherein said channel of said insertion tool defines a half-open channel.

32. The system of claim 30, wherein the spacer guide is at least one flange disposed on the rectangular channel of the insertion tool.

33. The system of claim 30, wherein the spacer guide is at least one rib longitudinally disposed on the inner surface of the rectangular channel of the insertion tool.

34. The system of claim 30, wherein the spacer guide is a protrusion on the inner surface of the rectangular channel of the insertion device.

35. The system of claim 30, wherein the spacer guide comprises a plurality of protrusions on the inner surface of the rectangular channel of the insertion device.

36. The system of claim 30, wherein the distal end of the pusher is configured to receive the vertebral spacer.

37. A system for delivering a vertebral spacer to the spinal column of a patient, comprising:
   (a) an insertion tool for delivering a vertebral spacer to the spinal column of a patient, comprising a channel having an inner surface;
   (b) a pusher having a distal end is slideably disposable in the channel of the insertion tool;
   (c) a vertebral spacer slideably disposable in the channel of the insertion tool; and (d) a cutting tool having a shaft with a distal end and a proximal end, and a cutting head secured to the distal end of the shaft, wherein the cutting tool is slideably disposable in the insertion tool providing that the pusher and the vertebral spacer are not disposed therein;

wherein the cutting tool further comprises a striking head connected to the proximal end of the shaft.

38. The system of claim 37, wherein the channel is a rectangular channel.

39. A method for delivering a vertebral spacer into a patient, comprising the steps of:

(a) inserting an insertion tool into an intervertebral space of the spinal column of a patient;

(b) engaging at least a first guiding groove of a vertebral spacer with a spacer guide of the insertion tool;

(e) urging, using a pusher, the vertebral spacer into the intervertebral space and thereby into a vertebral spacer receiving slot defined in a vertebra of the patient; and (d) removing the pusher and the insertion tool from the patient.

40. The method of claim 39, wherein the insertion tool is rotated into a position substantially normal to a vertebra.

41. The method of claim 39, further comprising the steps of:

(c) inserting a guide tool into a selected position in an intervertebral space;

(f) sliding the insertion tool along the guide tool;

(g) directing the insertion tool to the selected position in an intervertebral space; and (h) removing the guide tool from the insertion tool.

42. The method of claim 39, further comprising the steps of:

(c) sliding a cutting tool in the insertion tool;

(f) contacting a vertebra with the cutting tool;

(g) cutting a vertebral spacer receiving slot in the surface of the vertebra defining the intervertebral space;

(h) removing the cutting tool from the patient; and (i) pushing the vertebral spacer into the vertebral spacer receiving slot of the vertebra.

43. The method of claim 42, further comprising the steps of repeating steps (e)–(i), thereby delivering a second vertebral spacer to the intervertebral space.

44. The method of claim 39, wherein the vertebral spacer is a section from the shaft of a femur having a portion of a femur medullary cavity and further comprising the step of delivering a hardening biocompatible composition to said femur medullary cavity.

45. The method of claim 44, wherein the hardening biocompatible composition comprises a bone composition, an organic polymer, methyl methylacrylate, an osteogenic composition or a combination thereof.

46. The method of claim 44, herein the hardening biocompatible composition comprises hydroxyapatite.

47. The method of claim 39, wherein the insertion tool has a first cross-sectional dimension and has a second cross-sectional dimension narrower than the first cross-sectional dimension, and further comprising the step of rotating the insertion tool after it has been inserted into an intervertebral space.

* * * * *